United States Patent [19]

Hastings et al.

[11] 4,061,756
[45] Dec. 6, 1977

[54] METHODS FOR TREATING CARDIOVASCULAR DISORDERS

[75] Inventors: Stephen G. Hastings, Chelsea; Bruno P. H. Poschel; Donald E. Butler, both of Ann Arbor, all of Mich.

[73] Assignee: Parke, Davis & Company, Detroit, Mich.

[21] Appl. No.: 751,829

[22] Filed: Dec. 17, 1976

[51] Int. Cl.$^2$ .............................................. A61K 31/44
[52] U.S. Cl. ................................. 424/263; 260/297 R
[58] Field of Search ..................... 424/263; 260/297 R

[56] References Cited

U.S. PATENT DOCUMENTS

3,429,689   2/1969   Duerr ............................... 260/297 R

OTHER PUBLICATIONS

Chem. Abst., vol. 75 (1971)-76545a.
Butler et al., J. of Med. Chem, vol. 14, No. 7, pp. 575–579 (1971).

*Primary Examiner*—Stanley J. Friedman
*Attorney, Agent, or Firm*—Stephen Raines; David B. Ehrlinger; Frank S. Chow

[57] ABSTRACT

Methods for treating certain cardiovascular disorders by administering 3-phenoxypyridine or a pharmaceutically acceptable acid-addition salt thereof.

5 Claims, No Drawings

METHODS FOR TREATING CARDIOVASCULAR DISORDERS

SUMMARY AND DETAILED DESCRIPTION

The present invention relates to methods for treating cardiovascular disorders in mammals, such as dogs, horses, sheep, etc., by administering 3-phenoxypyridine or a pharmaceutically acceptable acid-addition salt thereof.

The term "cardiovascular disorders" is intended to mean acute cardiogenic shock, myocardial ischemia and drug induced myocardial depression, such as that caused by barbiturates or other depressant agents.

The term "pharmaceutically acceptable acid-addition salt" is intended to mean any salt form that is prepared from a relatively non-toxic acid, such as hydrochloric acid, sulfuric acid, P-toluene sulfonic acid, benzoic acid, citraconic acid, maleic acid, etc. The preferred compound is 3-phenoxypyridine monosulfate, which is prepared from equimolar amounts of 3-phenoxypyridine and sulfuric acid.

In addition, the 3-phenoxypyridine and its pharmaceutically acceptable acid-addition salts can exist in anhydrous forms as well as in solvated, including hydrated, forms. In general, the hydrated forms and the solvated forms with pharmaceutically acceptable solvents are equivalent to the anhydrous or unsolvated form for the purposes of the invention. A typical hydrate would be the aforementioned hydrochloride in the form of its hydrate.

In addition, 3-phenoxypyridine compounds may exist in more than one crystalline form, such as the monosulfate, m.p. 114.5°–117° C. and m.p. 107°–109° C., and all forms are intended to be included within the scope of this invention.

While 3-phenoxypyridine or its acid-addition salts may be administered orally, it is preferably administered parenterally, with the dosage adjusted to the needs and tolerances of the individual patient. Of the numerous parenteral routes, the intravenous route is most preferred. The usual mammalian parenteral dosage range for a 70 kg. human subject is from 14.0 to 2,100 mg. per day (.2 mg. to 30.0 mg. per kg. of weight per day), preferably 70 to 700 mg. per day (1.0 mg. to 10.0 mg. per kg. of weight per day), optionally in divided portions.

The above employed pharmaceutical compositions are produced by formulating a compound of the foregoing formula (as an active ingredient) in dosage unit form with a pharmaceutical carrier. Some examples of dosage unit forms are tablets, capsules, lozenges, and pills; as well as powders and aqueous and non-aqueous oral solutions and suspensions and parenteral solutions packaged in containers containing either one or some larger number of dosage units and capable of being subdivided into individual doses by such means as measurement into a teaspoon or other standard container. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerine, sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present. The compositions of the invention preferably contain from 10 to 2,000 mg. of the active ingredient per dosage unit so that the entire amount to be administered during a day can be made up from a reasonable number of dosage units.

The invention is illustrated by the following example:

EXAMPLE

Six adult mongrel dogs of either sex, weighing 12—20 kg. are anesthetized. The animals are premedicated with morphine sulfate, 2 mg./kg. (intramuscular) and then anesthetized with sodium pentobarbital 35 mg./kg. (intravenous). Respiration is maintained using a respirator and blood gas and pH are monitored and maintained at normal values. Thoracotomy is performed through the 4th left intercostal space for placement of an aortic electromagnetic flow probe at the origin of the aorta and a Konigsberg pressure transducer in the left ventricle via the left atrium. The thorax is then closed and the femoral artery and vein cannulated for blood pressure measurement and drug injection, respectively. Electrodes are placed for lead II EKG.

To evaluate the effects of 3-phenoxypyridine monosulfate on cardiovascular function, the following primary signals are recorded: aortic blood flow, aortic blood pressure, left ventricular blood pressure, and electrocardiogram. Aortic blood flow is measured with an electromagnetic flow probe coupled to a blood flowmeter while aortic blood pressure is obtained using a pressure transducer. The transducer is located at phlebostatic level and the implanted catheter extended directly to the transducer. Transducer couplers are used for conditioning both pressure signals and electrocardiograms are recorded from the electrodes using an amplifier with a low frequency cut off of 0.05 Hz.

For assessment of cardiovascular performance, analog signals are recorded on polygraph and simultaneously digitized and processed by a computer system. Electrocardiogram traces are visually scanned for possible drug effects. The primary cardiovascular parameters which are obtained include heart rate, systolic and diastolic aortic blood pressure, stroke volume, and peak aortic flow. Derived parameters are maximum left ventricular dp./dt., maximum first derivative of aortic flow, cardiac output, mean blood pressure, and calculated total peripheral resistance.

Prior to drug administration, an adequate control period is obtained. The 3-phenoxypyridine monosulfate is then injected (intravenous) through the femoral cannula. Animals are monitored for 45 minutes between each dose (the following doses are given, calculated as free base).

0.2 mg./kg. in 0.9% NaCl, 0.5 mg./ml. pH 7.4

0.4 mg./kg. (cumulative 0.6 mg./kg.), in 0.9% NaCl, 0.5 mg./ml., pH 7.4

1.4 mg./kg. (cumulative 2.0 mg./kg.), in 0.9% NaCl, 5.0 mg./ml. pH 3.6

4.0 mg./kg. (cumulative 6.0 mg./kg.), in 0.9% NaCl, 5.0 mg./ml., pH 3.6

Control studies are also done on 3 dogs, injecting the vehicle (0.9% NaCl) at the appropriate volume and pH, at the corresponding times.

It is found that the threshold dose of 3-phenoxypyridine monosulfate producing cardiovascular effects in the anesthetized dogs is 0.6 mg./kg. (cumulative) with pronounced effects seen at 2.0 and 6.0 mg./kg. (cumulative). The cardiovascular changes produced by the compound are slow in onset, achieving near maximum effect by 45 minutes which plateaued for 2 hours after the last dose. 3-Phenoxypyridine monosulfate causes a marked positive inotropic effect as demonstrated by an increase in stroke volume (+38%), maximum 1st derivative of left ventricular pressure (+145%), peak aortic flow rate (+54%) and its 1st derivative (+107%). In addition, cardiac output increases 26 % with little change in total peripheral resistance, resulting in a 30-35% increase in blood pressure, with systolic pressures often above 200 mm. Hg. while heart rate is minimally affected. Control animals receiving vehicle only show no change in cardiovascular performance during the course of the experiment. These effects are seen after acute administration of the compound. Following repeat administration of the compound, pharmacological tolerance develops as evidences by an attenuated response.

The following are parenteral formulations that may be used in this invention:

A 3-phenoxypyridine 2 mg.
Phemerol Chloride Recrystallized 0.1 mg.
Hydrochloric acid qs ad pH 1.2
Water for Injection USP qs ad 1.0 ml.

The phenoxypyridine is mixed with about two-thirds of the required volume of Water for Injection USP followed by the addition of Phemerol Chloride. Hydrochloric acid of appropriate normality is added slowly to produce a pH of 1.2 followed by the addition of sufficient Water for Injection to reach the desired volume.

After mixing, checking the pH and adjusting if necessary, the solution is sterilized by membrane filtration (a 0.22 micron Millipore filter membrane represents a suitable filter). The desired quantity of above prepared solution is filled into appropriate size multiple dose vials suitable for injectable preparations and stopper with gum rubber or suitable butyl rubber closures and sealed with aluminum ferrules. The preparation may also be filled into suitable size single dose glass ampoules and sealed.

Using the above procedure, solutions containing 5, 10 25, 50 or 100 mg./ml. of 3-phenoxypyridine may be prepared.

B 3-phenoxypyridine monosulfate 3.14 mg.
Phemerol Chloride Recrystallized 0.1 mg.
Water for Injection USP qs ad. 1.0 ml.

The Phemerol Chloride is dissolved in about two-thirds of the required volume of Water for Injection USP. The 3-phenoxypyridine monosulfate is added and the mixture is stirred until the solution is clear. After enough water is added to make the required volume, a solution having 2 mg. of active material calculated on the free base is obtained. The solution is sterilized and ampoules filled in the same manner as shown above.

By using the 7.86 mg., 15.72 mg., 39.30 mg., 78.60 mg., and 157.23 mg. of 3-phenoxypyridine monosulfate in the above formulation, one obtains a formulation with the equivalent amount of phenoxypyridine per ml. of solution, 5 mg., 10 mg., 25 mg., 50 mg., and 100 mg., respectively.

We claim:

1. A method for treating cardiovascular disorders in a mammal which comprises administering an effective amount of 3-phenoxypyridine or a pharmaceutically acceptable acid-addition salt thereof to a mammal suffering from cardiovascular disorders.

2. The method of claim 1 wherein .2 mg./kg. to 30 mg./kg. per day of said compound is administered.

3. The method of claim 1 wherein said cardiovascular disorder is acute cardiogenic shock.

4. The method of claim 1 wherein said cardiovascular disorder is myocardial ischemia.

5. The method of claim 1 wherein said cardiovascular disorder is drug induced myocardial depression.

* * * * *